United States Patent [19]
Owens et al.

[11] Patent Number: 6,017,564
[45] Date of Patent: Jan. 25, 2000

[54] TREATMENT OF STRESSED ANIMALS WITH DIHYDROXYQUINOLINE COMPOUNDS

[75] Inventors: Fredric Newell Owens, Stillwater, Okla.; Winston A. Samuels, Chesterfield, Mo.

[73] Assignee: Solutia Inc., St. Louis, Mo.

[21] Appl. No.: 09/138,213

[22] Filed: Aug. 21, 1998

Related U.S. Application Data

[60] Provisional application No. 60/081,788, Apr. 14, 1998.

[51] Int. Cl.$^7$ ...................................... A23K 1/00
[52] U.S. Cl. .............................. 426/2; 426/807
[58] Field of Search ........................ 426/2, 807

[56] References Cited

U.S. PATENT DOCUMENTS

| | | |
|---|---|---|
| 4,079,153 | 3/1978 | Coleman . |
| 4,087,561 | 5/1978 | Bharucha et al. . |
| 4,088,793 | 5/1978 | Bharucha et al. . |
| 4,305,932 | 12/1981 | Menachemoff et al. .............. 424/180 |
| 4,592,915 | 6/1986 | Goyette et al. . |
| 4,871,551 | 10/1989 | Spencer . |
| 4,952,590 | 8/1990 | von Magius . |
| 4,986,996 | 1/1991 | Barlow et al. . |
| 5,000,964 | 3/1991 | McCauley, III . |
| 5,066,498 | 11/1991 | McCauley, III . |
| 5,167,835 | 12/1992 | Harder . |
| 5,282,379 | 2/1994 | Harder et al. . |

FOREIGN PATENT DOCUMENTS

| | | |
|---|---|---|
| 943962 | 3/1974 | Canada . |
| 944135 | 3/1974 | Canada . |
| 2087792 | 1/1993 | Canada . |
| 0 466 674 A1 | 1/1992 | European Pat. Off. . |
| 2513491 | 9/1981 | France . |
| 2921 | 11/1977 | Hungary . |
| 46036625 | 2/1969 | Japan . |
| 48012744 | 5/1970 | Japan . |
| 51-024421 | 7/1976 | Japan . |
| 58-031944 | 2/1983 | Japan . |
| 631517 | 11/1978 | U.S.S.R. . |
| 649396 | 2/1979 | U.S.S.R. . |
| 679578 | 8/1979 | U.S.S.R. . |
| 705334 | 12/1979 | U.S.S.R. . |
| 751381 | 7/1980 | U.S.S.R. . |
| 955316 | 4/1964 | United Kingdom . |
| 1356002 | 6/1974 | United Kingdom . |
| 1440183 | 6/1976 | United Kingdom . |
| 1444024 | 7/1976 | United Kingdom . |
| 1537334 | 12/1978 | United Kingdom . |
| WO 9503712 | 2/1995 | WIPO . |

OTHER PUBLICATIONS

Cielens et al., Latv. PSR Zimet. Akad. Vestis, vol. 11, pp. 54–60, 1974.

Nicholson et al., Effect of Mash Or Pelleted Supllements Containing Crab Meal On Intake And Weight Gains Of Beef Cattle, *Canadian Journal Of Animal Science*, 76(1):95–103 (1996) (Abstract Only).

Herrick, Feed Additives And Their Uses In Cattle, *Feedstuffs, USA*, 44(43):A20–A22, (1972) (Abstract Only).

Smekalov et al., Use of Meat Factory By–Products In Whole Milk Substitutes For Calves, *Zhivotnovodstvo*, 11:42–54, (1979) (Abstract Only).

Lauridsen et al., Comparative Studies On The Effect Of Butylhydroxy–Toluene And Ethoxyquin On The Antioxidative And Oxidative Balance In Broilers, *J. Anim. Physiol. Anim. Nutr.*, 72(1):26–37, (1994) (Abstract Only).

Gatlin, III et al., Effects Of Dietary Vitamin E And Synthetic Antioxidents On Composition And Storage Quality Of Channel Catfish, Ictalurus Punctatus, *Aquaculture*, 106(3–4):323–332 (1992) (Abstract Only).

Bartov et al., Effects Of High Concentrations Of Dietary Vitamin E And Ethoxyquin On The Performance Of Laying Hens, *Br. Poult. Sci.*, 32(3):525–534, (1991) (Abstract Only).

Huang et al., Effect Of Dietary Fish Oil On Omega –3 Fatty Acid Levels In Chicken Eggs And Thigh Flesh, *J. Agric. Food Chem.*, 38(3):743–747, (1990) (Abstract Only).

Bharucha et al., Nitroxides Derived From Ethoxyquin And Dihydroethoxyquin As Potent Antinitrosamine Agents For Bacon, *J. Agric. Food Chem.*, 35(6):915–917, (1987) (Abstract Only).

Shahidi et al., Control Of Lipid Oxidation In Cooked Ground Pork With Antioxidents And Dinitrosyl Ferrohemochrome, *J. Food Sci.*, 52(3):564–567, (1987) (Abstract Only).

Bharucha et al., P–Alkoxyanilines As Antinitrosamine Agents For Bacon, *J. Agric. Food Chem.*, 34(5):814–818, (1986) (Abstract Only).

Bartov et al., Effect Of Dietary Vitamin E On The Stability And Sensory Quality Of Turkey Meat, *Poult. Sci.*, 62(7):1224–1230, (1983) (Abstract Only).

Bartov et al., Stability Of Abdominal Fat And Meat Of Broilers: Combined Effect Of Dietary Vitamin E And Synthetic Antioxidants, *Poutl. Sci.*, 60(8):1840–1845, (1981) (Abstract Only).

Bartov et al., Lack Of Effect Of Dietary Ascorbin Acid On Stability Of Carcass Fat And Meat Of Broilers, *Br. Poult. Sci.*, 18(5):553–555, (1977) (Abstract Only).

Bartov et al., Stability Of Abdominal Fat And Meat Of Broilers: Relative Effects Of Vitamin E, Butylated Hydroxytoluene And Ethoxyquin, *Br. Poult. Sci.*, 18(1):59–68, (1977) (Abstract Only).

Dahle et al., Gas Chromatographic Determination Of Ethoxyquin In Feed And Food Products, II, *J. Agric. Food Chem.*, 23(6):1093–1095, (1975) (Abstract Only).

(List continued on next page.)

*Primary Examiner*—Chhaya D. Sayala
*Attorney, Agent, or Firm*—Howell & Haferkamp, L.C.

[57] ABSTRACT

The collective health, feed efficiency, weight gain and fecal odors of stressed ruminant mammals can be improved by feeding them a diet of feed comprising a substituted 1,2-dihydroquinoline compound.

21 Claims, No Drawings

OTHER PUBLICATIONS

Evitomova et al., Effect Of Feed Mixtures With Stabilized And Nonstabilized Animal Fat Used After Storage, For Fattening Pigs, *Zhivotnovud, Nauki,* 12(3):48–55, (1975) (Abstract Only).

Webb et al., Effects Of Feeding Antioxidants On Rancidity Development In Pre–Cooked, Frozen Broiler Parts, *Poult. Sci.,* 51(5):1601–1605, (1972) (Abstract Only).

King et al., Alpha–Tocopherol, .Beta.–Carotene And Ascorbic Acid As Antioxidants In Stored Poultry Muscle, *J. Food. Sci.,* 60(5):1009–1012, (1995) (Abstract Only).

Shanhidi et al., Evaluation Of Malonaldehyde As A Marker Of Oxidative Rancidity In Meat Products, *J. Food Biochem.,* 15(2):97–105, (1991) (Abstract Only).

Bharucha et al., Ethoxyquin, Dihydroethoxyquin, And Analogs As Antinitrosamine Agents For Bacon, *J. Agric. Food Chem.,* 33(5):834–839, (1985) (Abstract Only).

Pikul et al., Effect Of Antioxidants On The Stability Of Mechanically Deboned Frozen Poultry Meat, *Fleischwirtschaft,* 63(5):960–964, (1983) (Abstract Only).

Jasiunas, Use Of Antioxidants In Feed Mixes For Meat–Poultry, *Nauch. Tr. Pribalt. Zonal. Opyt. St. po Ptitsevod.,* (8):52–55, From: Ref. Zh., Zhivotnovod, Vet. 1984, Abstr. No. 458614, (1983) (Abstract Only).

Combs et al., Influence Of Selenium, Vitamin E, And Ethoxyquin On Lipid Peroxidation In Muscle Tissues From Fowl During Low Temperature Storage, *Poult. Sci.,* 59(2):347–351, (1980) (Abstract Only).

Dvinskaya et al., Content Of Ethoxyquin In Chick Tissues, *Veterinariya* (Moscow), 11:73–74, (1979) (Abstract Only).

Bartov et al., Nutritional Factors Affecting The Carcass Quality Of Broilers, *Proc.–Ga. Nutr. Conf. Feed Ind.,* 44–55, (1979) (Abstract Only).

Coleman, A Model System For The Formation Of N–Nitrosopyrrolidine In Grilled Or Fried Bacon, *J. Food Technol.,* 13(1):55–69, (1978) (Abstract Only).

Dvinskaya, Effect Of Qualitively Different Fats, .Alpha–Tocopherol, And Antioxidants On Morphofunctional Changes In Tissues, Vitamin Requirement And Productively Of Broiler Chicks, *Tr. Vses. Nauchno–Issled. Inst. Fiziol., Biokhim, Pitan, S–kh. Zhivotn.,* 17:134–149, (1977) (Abstract Only).

Piul'Skaya et al., Oxidative Changes Of Meat–Bone Meal During Storage And The Effect Of Antioxidants, *Tr., Vses. Nauchno–Issled. Inst. Myasn. Prom–Sti.,* 39:3–9, (1977) (Abstract Only).

Kanid'ev et al., First Soviet Polybitamin Premix For Trout, *Rybn. Khoz.* (Moscow), 11:12–14, (1976) (Abstract Only).

Peterson et al., Vitamin E And Fishy Off–Flavors In Turkey Meat, *Qual. Polut. Meat, Proc. Eur. Symp.,* $2^{nd}$(31A):8, (1975) (Abstract Only).

Katkevicius et al., Effect Of Different Doses Of The Antioxidant Diludin On The Growth Of Meat Pullets, *Kompleksn. Ispol'z. Biol. Akt. Veshchestv Korml. S–kh. Zhivotn., Mater. Vses. Soveshch.,* $1^{st}$ Meeting Date 1973, 390–394, Editor(s): Solntsev, K.M. Publisher: Beloruss. S–kh. Akad., Gorki, USSR, (1974) (Abstract Only).

Grigorov et al., Effect Of Santoquin On The Preservation Of Carotene In A Microbial Preparation, *Zhivotnovodstvo,* (12):48–49, (1974) (Abstract Only).

Piul'Skaya et al., Use Of Santoquin–Stabilized Meat–And–Bone Meal In the Feeding Ration Of Pigs, *Tr., Vses. Nauchno–Issled. Inst. Myasn. Prom–sti.,* 29:43–46 CODEN: TVMYAE, (1974) (Abstract Only).

Kogan, Effect Of Vitamin E, Santoquin, And Sodium Selenite On Broiler Performance, *Aktual. Probl. Razvit. Ptitsevod.,* 6:162–169, (1973) (Abstract Only).

Astrup, Vitamin E And The Quality Of Pork *Acta Agr. Scand., Suppl.,* 19:152–157, (1971) (Abstract Only).

Kirkland et al., Effect Of Ethoxyquin On The Chemical And Nutritional Changes Of Poultry, By–Product Meal And Poultry Offal Fat During Storage, *Poultry Sci.,* 50(1):137–143, 91971) (Abstract Only).

Opstvedt Antioxidant–Stabilized And Solvent–Extracted Fish Meal In Diets For Broiler Chickens With Different Levels Of Added Vitamin E And 6–Ethoxy–1, 2–Dihydro–2, 2,4–Trimethylquinoline, *Acta Agr. Scand.,* 21(2):125–143, (1971) (Abstract Only).

Spruzs, Stabilizing Effect Of Ethoxyquin And Diludien On The Carotene In Grass meal And Mixed Feed, *Regul. Rosta Metab. Zhivotn.,* 111–124, Editor(s): Valdmanis, A. Publisher: "Zinatne", Riga, Latv, SSR, (19710 (Abstract Only).

Totev et al., Preservation Of Pork Cracklings Stabilized With Antioxidants, *Zhivotnovud. Nauki,* 8(5):55–61, (1971) (Abstract Only).

Zabara, Enrichment Of The Rations Of Young Hogs With Stabilized Carotene Of Grass Meal, *Svinovodstvo (Kiev),* 15:35–40, (1971) (Abstract Only).

Opstvedt et al., Influence Of Residual Lipids On The Nutritive Value Of Fish Meal. II. Effects on Carcass Composition And Organoleptic Quality Of Different Levels Of Antioxidant Stabilized And Unstabilized Fish Meal In Broiler Diets With And Without Added Vitamin E, *Acta Agr. Scand.,* 20(3):185–193, (1970) (Abstract Only).

Spruzs, Effectiveness Of Mixed Feed With Carotene–Stabilized Grass Meal In Bacon Pig Fattening, *Nauka–Zhivotnovod,* (8):109–115, (1970) (Abstract Only).

Kirkland et al., Effect Of Ethoxyquin On The Nutritional Value Of Animal Byproducts, *Feedstuffs,* 42(11):17–18, 20, (1970) (Abstract Only).

Van Deren et al., Collaborative Study Of The Determination Of Ethoxyquin In Chick Tissue And Eggs By Fluorescence, *J. Assoc. Offic. Anal. Chem.* 51(3):537–539 (1968) (Abstract Only).

Van Deren et al., Collaborative Study Of The Determination Of Ethoxyquin In Chick Tissue And Eggs, *J. Assoc. Off. Anal. Chem.,* 50(4):844–847, (1967) (Abstract Only).

Neudoerffer et al., Effects Of Dietary Polyunsaturated Fatty Acids On The Composition Of The Individual Lipids Of Turkey Breast And Leg Muscle, *Br. J. Nutr.,* 21(3):691–714, (1967) (Abstract Only).

Loury et al., Prevention Of Fat Oxidation. IV. Conservation Of Suets Subsequently Used In The Preparation Of Artificial Milk, *Rev. Fr. Corps Gras,* 14(11):645–647, (1967) (Abstract Only).

Synowieszki et al., Effect Of An Antioxidant On The Stability Of Vitamin A In Mineral–Vitamin Preparations And Concentrates Forming Part Of Feed Mixtures, *Med. Welt,* 23(9):523–525, (1967) (Abstract Only).

Sathe et al., Nutritional Evaluation Of Meat Meals For Poultry. V. Effect Of Addition Of Antioxidants During And After Processing On Growth–Promoting Value Of High And Low Quality Meat Meals, *Aust. J. Agric. Res.,* 18(1):183–191, (1967) (Abstract Only).

Javeed Ahmed et al., Growth And Meat Quality Of Broiler Chicks Fed With Fermented Fish Viscera Silage, *International Journal Of Animal Sciences,* 11(1):1–5, 19 ref. (1996) (Abstract Only).

Kobakhidze et al., Therapeutic And Prophylactic Feed Preparation For Broiler Chicks, *Farmakologicheskie I Toksikologicheskie Asperkty Promyshlennogo ZHibotnovodstva* 68–70. Sbornik Nauchnykh Trudov Moskovskai Veterinarnoi Akademii, (1985) (Abstract Only).

Hobson–Frohock, Residues Of Ethoxyquin In Poultry Tissues And Eggs, *Journal Of THe Science Of Food And Agriculture,* 33(12):1269–1274, 10 ref. (1982) (Abstract Only).

Karadzhyan et al., Effect Of Some Antioxidants On Egg Yield Of Hens And Lipid Content Of Their Tissues, *Trudy Erevanskogo Zootekhinichesko–Veterinarnogo Institute,* 50:172–176, 91981) (Abstract Only).

Zhekov et al., Study On The Biological Activity Of Vitamin E In Forage Mixtures Of Different Santoquin Content, Prouchvaniya V Rkju BIoilogichnata Aktivnost Na Vitamin E V V Furazhni Smeski S Razlichno S d rzhanie Na Santokvin, *Veterinarnomeditsinski Nauki,* 18(1):77–83 15 ref. (1981) (Abstract Only).

Bartov, Pro–And Antioxidants In The Diets Of Broilers And Their Effects On Carcass Quality: Copper, Selenium And Acidulated Soybean–Oil Soapstock *Poultry Science,* 56(3):829–835, (1977) (Abstract Only).

Spruzh, Diludin And Santoquin For Fattening Pigs, *Svinovodstvo, Moscow, USSR,* (2):18–19, (1975) (Abstract Only).

Kogan, Vitamin E And Santoquin For Rearing Broilers, *Khimiya V Sel' Skom Shozyaistve,* 11(6):462–463, ISSN: 0023–1185, (1973) (Abstract Only).

Atkinson et al., Flavour Studies With Different Levels And Times Of Fish Meal Feeding And Some Flavour–Imprating Additives In Broiler Diets, *Agroanimalia,* 4(2):53–61, (1972) (Abstract Only).

Combs et al., Influence Of Selenium, Vitamin E, And Ethoxyquin On Lipid Peroxidation In Muscle Tissues From Fowl During Low Temperature Storage, *Poultry Science,* 59(2):347–351, 26 ref. (1980) (Abstract Only).

Sirbu et al., Effect Of Some Premix Racipes With Different Vitamin Contents On Egg And Meat Production Of Meal–Line Hens, *Lucrarile Stiintifice ALe Institutului de Cercetari Pentru Nutritia Animalelor,* 5:201–209, 26 ref. (1976) (Abstract Only).

Kronka et al., Beef Tallow In Pig Feeding And Its Effects On Growth, Carcass Quality And Chemical Composition Of Backfat, *Cientifica,* 2(2):189–197, 20 ref. (1974) (Abstract Only).

Rojas et al., Effects Of Peruvian Anchovy (Engraulis Ringens) Meal Supplemented With Santoquin On Growth And Fishy Flavour Of Broilers, *Poultry Science,* 48(6):2045–2052, 23 ref. (1969) (Abstract Only).

Janssen et al., Gizzard Erosion Meat Flavor And Vitamin E In Broilers, *Acta Agric Scand Suppl.,* 19:72–78, (1973) (Abstract Only).

Christmas et al., The Performance Of Commercial Broilers When Fed Various Levels Of Rendered Whole–Hen Meal, *Poultry Science,* 75(4):536–539, Publisher: Savoy II: *Poultry Science Association, Inc.,* (1969) (Abstract Only).

Huang et al., Effect Of Dietary Fish On Omega–3 Fatty Acid Levels In Chicken Eggs And Thigh Flesh, *Journal Of Agricultural And Food Chemistry,* 38(3):743–747, (1990) (Abstract Only).

Combs, et al., Influence Of Selenium, Vitamin E, And Ethoxyquin On Lipid Peroxidation In Muscle Tissues From Fowl During Low Temperature Storage (Rancidity In Frozen Poultry, Meat), *Poultry Science,* 59(2):347–351 III, (1980) (Abstract Only).

TREATMENT OF STRESSED ANIMALS WITH DIHYDROXYQUINOLINE COMPOUNDS

This application claims the benefit of U.S. Provisional Application(s) No(s).: 60/081,788 Apr. 14, 1998.

BACKGROUND OF THE INVENTION (1) Field of the Invention

The present invention relates to treatment of animals with dihydroxyquinoline compounds, and more particularly to such treatment by application of such compounds to the feed of the animal.

(2) Description of the Prior Art

Animals that have been shipped, particularly over long distances, or deprived of food and/or water for a period of time commonly suffer stress, which often leads to a variety of afflictions. For example, calves often react poorly to their shipment to feed yards. In fact, usually most calves are sick when they arrive at the feed yard, suffering from a disease or other manner of ill-health. Typically the condition of the cattle is referred to as bovine respiratory disease (BRD). Because of their ill-health, upon arrival at the feed yard, the calves are placed into a pen, typically for about 45 to about 60 days, so that they may be segregated from the healthy cattle in the feed yard and nursed back to full health. Such newly arrived, segregated calves are termed "receiving cattle."

Due to the stress of shipment, receiving cattle tend to shrink during the shipment and perhaps 85% are sick when they arrive at the feedlot, or become sick, particularly with respiratory disease, soon after arrival. The receiving cattle tend to drink large quantities of water, but often tend not to get up and eat. Many require medication such as vaccines. Some even fail to recover from the sickness induced by the shipping stress, which sometimes results in death of calves. Thus, shipping produces undesirable stress and morbidity in the calves and contributes to higher medical costs and other costs associated with delays in return to health, loss of useable cattle due to disease and death, and reduced rate of weight gain and feed efficiency in the feed yard (i.e., weight gain per pound of feed). Accordingly, a treatment or other technique for accelerating restoration to health, increasing rate of weight gain, and reducing morbidity of the receiving cattle, and for reducing medical costs and improving feed efficiency would be highly desirable. In sum, the morbid cattle tend to require greater medical expense, to grow slower throughout the feedlot phase, are less efficient in converting feed to weight gain, and their carcasses tend to be graded lower after slaughter. Other ruminant mammals, such as sheep, suffer similarly from stress.

In addition, many meat products derived from ruminant mammals (such as, cattle and sheep), swine and fish have very limited shelf lives. After a relatively short period of time, the meat may turn color and become rancid (that is, develop an unacceptable smell or flavor or both). In short, it spoils. Shelf life for beef is typically measured as the length of time for the meat, in plastic trays, overwrapped with an oxygen-permeable polyvinyl chloride film, and displayed under fluorescent lighting (150 foot candles) at 4° C., to discolor; to turn brown or grey. This definition will be used herein to apply to other meat products as well.

By this measure, shelf life for beef, even if sealed from exposure to air, is about seven days from slaughter, after which it may turn from red to brown or grey and spoil. And, as limited as this shelf life is, because of shipping delays, less than ideal storage conditions and increased surface area resulting from cutting the meat into steaks, the typical marketable life of steak in the display case is substantially shorter—closer to twelve hours. Moreover, while the quality and freshness of steak or other meat is commonly evaluated by the color of the meat, color is not a reliable indicator of quality or freshness. Meat can turn brown or grey significantly prior to spoilage. Thus, large quantities of high quality, fresh meat becomes unmarketable and thus is wasted because of deceptively premature color change.

The resulting food waste and loss from spoilage associated with shelf life limitations amounts to billions of dollars in the U.S. alone. In fact, it has been estimated that increasing shelf life of beef in the supermarket by just two days could save the U.S. beef industry up to $175 million through increased beef sales. See Schaefer et al., Proc. Holstein Beef Prod. Symposium (1991), p. 175. The total value to the U.S. beef industry of increasing the shelf life of beef by just one to two days has been estimated at $1 billion. Hill, Ga. Stocker-Finnisher Conference (1992).

Thus, many efforts have been made toward increasing the shelf life of beef. Often the efforts have involved direct treatment of the beef, for example, with preservatives.

Other efforts, however, have been directed to treatment of the cattle themselves, such as supplementing their diets with chemical additives. With respect to cattle treatment by dietary intervention, research from the Universities of Wisconsin and Georgia indicates that adding 1200 to 1300 IU Vitamin E daily (100 ppm alpha-tocopherol acetate in the feed) to the diet of feedlot cattle extends the shelf life of several cuts of beef from a maximum of about seven days to about fourteen days or more. Williams et al., California Nutrition Conference (1993), pp. 23–42. It is believed that the Vitamin E increases the shelf life of beef—that is, maintains the meat color—by retarding the aging process by which metmyoglobin gradually replaces the red oxymyoglobin, causing the meat to become brown. However, the cost of this Vitamin E supplement is about 1.5 cents per animal a day, or $2.50 additional cost per animal. Because this cost is not recovered directly by the producer, it can be prohibitive. Nevertheless, completely satisfactory alternative dietary supplements are unknown. In fact, dietary techniques face long odds of success, at least in part with respect to ruminant mammals because many dietary ingredients are extensively destroyed during passage through the rumen. Even measurements with various commercial sources of Vitamin E indicated that intestinal availability was only 36 to 52% of that being fed. Shin and Owens, OK. State Univ. Animal Research Report, 154–158 (1990). Because shelf life extenders are so beneficial and alternatives are so limited, the use of Vitamin E is increasing dramatically despite its cost.

Although the addition of 6-ethoxy-1,2-dihydro-2,2,4-trimethylquinoline (commonly referred to as "ethoxyquin") to animal feeds as a dietary supplement to improve the shelf life of food products derived from animals consuming the feeds or to improve the health of stressed animals has nowhere even been suggested in the current art, its use as a feed ingredient for various reasons is well known. For example, because ethoxyquin is an antioxidant, it has been added to certain animal feeds to preserve the feed itself; that is, to prevent the feed constituents from spoiling. See, for example, U.S. Pat. Nos. 5,066,498 and 5,000,964, both to McCauley, III, which teach the use of up to 1.5% Santoquin® (an ethoxyquin composition sold by Solutia Inc.) to prevent oxidation and breakdown of certain components of a horse feed composition designed for treatment of the horse's hooves and coat. However, it is not clear that this use in feeds has resulted in ingestion of the ethoxyquin by the animals. It is reported in the background section of U.S. Pat. No. 4,986,996 to Barlow et al., that although ethoxyquin has been widely approved for use in animal feed and is the most commonly used anti-oxidant in fish meal intended for that use, within hours of the addition of the ethoxyquin to the feed, analyses of the feed no longer detect any trace of ethoxyquin. On the other hand, when ethoxyquin is ingested, tissue levels of ethoxyquin have been found to be similar whether calves had developed their rumen or not. deMille et al., Can. J. Anim. Sci. 52:351–361 (1972). Thus, even though many dietary ingredients are extensively destroyed during passage through the rumen, research to date suggests that ethoxyquin is not completely destroyed in the rumen. Indeed, it has been reported that addition of ethoxyquin to diets of dairy cattle has resulted in the appearance of ethoxyquin in the fat of the resulting milk. Dunkley et al., Supplementing Rations with Tocopherol and Ethoxyquin to Increase Oxidative Stability of Milk, J. Dairy Sci., Vol. 50, No. 4, pp. 492–499 (1967); Dunkley et al., Compounds in Milk Accompanying Feeding of Ethoxyquin, J. Dairy Sci., Vol. 51, No. 8, pp. 1215–1218 (1968).

Ethoxyquin also has been reported to have been used in a concentration of 0.05 to 0.1% (500–1,000 ppm) in a feed composition for breeding cattle with N3 fatty acid-accumulated beef. See Canadian Patent No. 2,087,792. According to page 10 of that Canadian patent, the ethoxyquin is used as an anti-oxidant and "also plays an anti-oxidation activity in the cattle's body, as well as in the feed composition, to prevent the oxidative decomposition of N3 fatty acid in spoilage of feed during long-term storage." And, in U.K., Pat. No. 144,024, the possible candidacy of ethoxyquin as an anti-oxidant component of a food or feed supplement to prevent the occurrence of or to retard cancer is reported. It is suggested there that the ethoxyquin concentration should be sufficient for the daily consumption to be about 0.01 to 500 mg.

Dietary ethoxyquin also has been applied to animals other than cattle. For example, it has been reported to reduce or to prevent certain maladies associated with a deficiency of Vitamin E, in particular, encephalomalacia, exudative diathesis in chicks, muscular dystrophy in chicks and lambs and fetal resorption in rats. It is unclear whether these effects have been direct effects on the target tissues or indirect effects through preventing lipid oxidation and reducing Vitamin E usage or by preventing Vitamin E destruction in the diet or the gut. Miller and White, Nutr. Rep. Int. 12:245–252 (1975); Whanger et al., Nutr. Rep. Inst. 13:159–173 (1976). However, dietary ethoxyquin has been reported to prevent lipid oxidation in muscle tissues in broilers and layers. Bartov and Bornstein, Br. Poultry Sci. 18:59–68 (1977); Combs and Regenstein, Poultry Sci. 59:347–351 (1980). The ethoxyquin concentration in the feed in the broiler study was 75 to 150 ppm by weight, and 150 ppm of ethoxyquin was found to be as effective as about 15 ppm alpha-tocopherol acetate. In the layer study, the ethoxyquin concentration was 500 ppm. Ethoxyquin was detected in the muscle tissue of poultry and lambs, suggesting that the effect is directly in the tissue. deMille et al., Can. J. Anim. Sci. 52:351–361 (1972).

Despite these reports of uses of ethoxyquin in feed, there is no indication that the ethoxyquin has had any effect on the shelf life of meat products derived from the animals or on the health of receiving cattle. In fact, ethoxyquin has been reported to be a direct food additive, but even that has been for purposes other than to increase shelf life of the food or to improve the health of stressed animals. For example, U.S. Pat. No. 4,079,153 to Coleman, U.S. Pat. No. 4,087,561 to Bharucha and Coleman and U.S. Pat. No. 4,088,793 to Bharucha, Rubin and Cross disclose methods for reducing formation of nitrosamines by applying ethoxyquin directly to the meat.

Thus, the livestock industry and particularly the cattle industry, is still searching not only for ways to improve the health of receiving cattle, but also for inexpensive and simple techniques for extending the shelf life of animal-derived food products, such as beef and milk.

Moreover, it is noteworthy that these industries encounter several other problems as well and if a further benefit of the cattle health and shelf life treatments is to alleviate some of these problems as well, the value of the treatment would be enhanced even more. Among these problems may be noted the offensive odor associated with animal waste (e.g., cattle and swine manure). In addition, cattle and sheep, in particular, have been afflicted with high rates of liver abscesses. Commercially, about 15–30% of livers from feedlot cattle are discarded, primarily due to presence of abscesses. Thus, a method that reduces the incidence of liver abscesses or lessens their severity also would be beneficial. In fact, it has been reported that in a small study 2,000 ppm ethoxyquin appeared to increase rate of liver regeneration in rats by 26 to 34%. See Gavino et al., Life Sci. 36:1771–1777 (1985). Also, meat from younger animals is typically more desirable than that from older animals. Therefore, a technique that can delay the maturity of an animal or at least the apparent maturity, would be desirable as well. In addition, a certain percentage of beef is dark in color initially and therefore becomes unmarketable regardless of its age. As a result, that percentage is simply waste. Thus, methods for reducing the incident of dark color beef would be desired as well. Finally, of course, faster and more efficient weight gain rates are always desirable.

SUMMARY OF THE INVENTION

The present invention, therefore, is directed to a novel method for treatment of stressed ruminant mammals to improve the collective health, feed efficiency or weight gain of the mammals, comprising feeding to the mammals a diet of feed comprising a substituted 1,2-dihydroquinoline compound of the formula

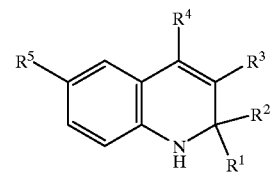

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms. The diet is continued for a period of time, and the feed comprises the substituted 1,2-dihydroquinoline compound in an amount, sufficient to improve the collective health, feed efficiency or weight gain of the mammals.

The present invention is also directed to a method for treating ruminant mammals undergoing a stress-inducing activity to inhibit morbidity resulting from the stress induced by the activity. The method comprises feeding to the mammals a diet of feed comprising a substituted 1,2-dihydroquinoline compound of the formula

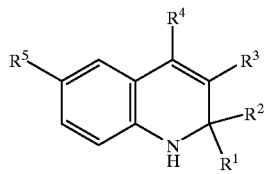

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms. The diet is continued for a period of time, and the feed comprises the substituted 1,2-dihydroquinoline compound in an amount, sufficient to inhibit morbidity resulting from the stress.

The present invention is further directed to a method for treatment of receiving cattle to improve the collective health, feed efficiency, weight gain or fecal odor of the receiving cattle. The method comprises feeding to the receiving cattle a diet of feed comprising a substituted 1,2-dihydroquinoline compound of the formula

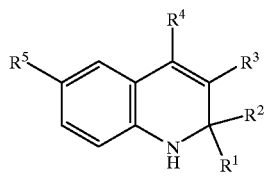

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms. The diet is continued for a period of time, and the feed comprises the substituted 1,2-dihydroquinoline compound in an amount, sufficient to improve the collective health, feed efficiency or weight gain of the receiving cattle.

Among the several advantages of this invention, may be noted the provision of a method for improving the collective health, feed efficiency, weight gain and fecal odors of stressed ruminant mammals; the provision of such method that involves merely simple, inexpensive and effective dietary treatment of the mammals; and the provision of such method that provides ancillary benefits as well.

DETAILED DESCRIPTION OF THE PREFERRED EMBODIMENTS

In accordance with the present invention, it has been discovered that feeding stressed mammals a diet of feed comprising a substituted 1,2-dihydroquinoline compound of the formula

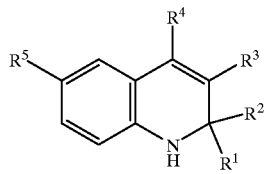

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, surprisingly improves the collective health, feed efficiency or weight gain of the mammals. "Stressed" mammals are mammals suffering adverse health effects such as sickness or diminished appetite as the result of an activity such as food or water deprivation or shipping of the mammals that causes such adverse health effects ("stress-inducing activities"). By improvement of "collective" health, feed efficiency or weight gain of the mammals, what is meant is an overall improvement for the group of mammals treated as opposed to a specified improvement for any particular preselected individual mammal from the group. "Improvement" in collective health, therefore, refers to reduced incidence of morbidity over what would be found for untreated stressed mammals. Likewise, "improvement" in collective feed efficiency or weight gain for the group refers to the average feed efficiency or weight gain, respectively, being increased over what would be found for similar stressed mammals that are untreated, and "improvement" in collective fecal odor refers to a reduction in the offensiveness in the odor of the mammals' feces over what would be found for similar stressed mammals that are untreated.

More particularly, it has been discovered that a feeding regimen that incorporates the substituted 1,2-dihydroquinoline compound into the feed of the receiving cattle for a period beginning shortly prior to shipment or, preferably, just after shipment of the calves to the feed yard (say, within a week after, preferably within two days after, optimally within a day after shipment) and extending for from about 14 to about 50 days, preferably about 14 to about 42 days, such as about 28 days, reduces the incidence of morbidity, including respiratory disease and liver abscesses, improves the feed efficiency and weight gain of the cattle, and reduces the degree of ofensiveness of the feces of the cattle.

It also has been discovered that the simple and relatively inexpensive incorporation of a substituted 1,2-dihydroquinoline compound into the diet of certain animals, particularly, ruminant mammals, such as cattle and sheep, swine and fish, surprisingly and substantially increases the shelf life of the meat products derived from them.

Moreover, the treatment of this invention has been found to provide several other benefits as well. For example, it also has been found that, surprisingly, the treatment appears to retard the aging process of the animal. As a result, the most desirable beef, i.e., youthful, lean-colored beef, may be obtained from cattle that otherwise are too old to be a source of such beef. Another surprising effect that has been discovered is a marked reduction in the offensive odor associated with the excretions of the cattle or other animals upon initiation of the treatment of this invention. In addition, it appears that the treatment of this invention also reduces the incidence of and/or lessen the severity of liver abscesses in the animals, particularly cattle, that are subjected to the treatment. Not only that, but the treatment of the invention has been found to reduce the incidence of dark color beef as well. And significantly—and surprisingly—the treatment has been found to lower the feed intake rate, while at the same time increase the weight gain rate of the animal despite the lower food intake. Feed efficiency is therefore enhanced.

In particular, the treatment of this invention for improving the shelf life of meat may be applied to ruminant mammals, such as cattle and sheep, to swine and, to fish. Of these animals, the treatment is most particularly designed for ruminant mammals and swine, especially ruminant mammals. Of the ruminant mammals, the treatment is envisioned as having greatest application to cattle, primarily cattle to be used for beef.

According to the treatment for stressed animals and for increasing shelf life of meat from the animals, the animals are fed their standard feed, except that a substituted 1,2-dihydroquinoline compound has been added to it. The substituted 1,2-dihydroquinoline compound corresponds to the formula

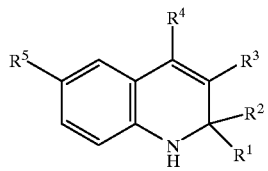

wherein $R^1$, $R^2$, $R^3$, and $R^4$ are independently selected from hydrogen and alkyl groups of from 1 to about 6 carbon atoms, preferably from 1 to four carbon atoms, and $R^5$ is an alkoxy group of from 1 to about 12 carbon atoms, preferably from 1 to four carbon atoms. The most preferred 1,2-dihydroquinoline is 6-ethoxy-1,2-dihydro-2,2,4-trimethylquinoline, commonly known as "ethoxyquin." Ethoxyquin is a well known compound, as discussed above, and is readily available. For example, one form is sold under the trademark SANTOQUIN®. The ethoxyquin may be added in wet or dry form. For the sake of brevity, the following description of the method of this invention will refer specifically to ethoxyquin, but it should be understood that it is believed that the method may be generalized to the other 1,2-dihydroquinolines defined above as well.

Because ethoxyquin may tend to oxidize over time upon exposure to the other feed constituents, it is preferred that it be mixed with the other feed components shortly before the animal feeding, preferably within a day of feeding, more preferably within two hours of feeding. No further additives, such as N3 fatty acids, are required. And, whereas conventional use of ethoxyquin to prevent rancidity or spoilage of the feed itself involved addition of the ethoxyquin only to the fat or tallow ingredients of the feed, such as fish meal, in the present method, ethoxyquin is added even to the non-fat ingredients of the feed. While the ethoxyquin might be present in less than all the ingredients initially, it is desired that the ethoxyquin be dispersed through all the ingredients of the finished feed. This addition may be in combination with the mixing together of the feed ingredients to form the feed, or after the mixing of the after ingredients. In the former case, the ethoxyquin may be simply mixed in as another feed ingredient. In the latter case, the ethoxyquin may be sprayed on the feed mixture, for example, if the ethoxyquin is in liquid form, or mixed into the feed mixture.

For improving the shelf life of the meat from the animal, the ethoxyquin should be incorporated into the feed in an amount sufficient, that when fed to the animal for the desired length of time, the shelf life of the food product derived from the animal is extended. For treating stressed mammals, the ethoxyquin should be incorporated into the feed in an amount sufficient, that when fed to the animal for the desired length of time, sufficient to improve the collective health, feed efficiency, weight gain and fecal odor of the mammals. For example, in the case of cattle, it has been found that the shelf life of the beef derived from the cattle may be extended from a conventional three to seven days to ten to fourteen days with an ethoxyquin concentration in the feed of from about 25 to 1,000 ppm by weight or more, preferably from about 50 to about 500 ppm by weight, more preferably from about 50 to about 200, even more preferably from about 100 to about 200 ppm by weight, and optimally from about 100 to about 150 ppm by weight. These concentrations are based on the weight of feed in terms of dry feed intake, as is standard in the industry for referring to concentration. The particular optimum level of ethoxyquin depends in part on the type of feed, with, for example, high vegetable oil level feed requiring higher levels of ethoxyquin. The same concentrations also have been found to improve the collective health, feed efficiency, weight gain and fecal odor of the mammals.

Surprisingly, the ranges of ethoxyquin concentrations found most desirable for the present method falls between the ethoxyquin concentrations typically employed for preservation of feed (up to, perhaps, 1,000 ppm by weight in the fat, which in turn ordinarily makes up about 5% of the feed, corresponding to an ethoxyquin concentration in the feed of up to about 50 ppm by weight) and the ethoxyquin concentration called for in practicing the method of the Canadian Patent No. 2,087,792 (0.05% to 0.1%, which corresponds to 500 to 1,000 ppm by weight). Not only that, but the optimal range, particularly 100 to 150 ppm by weight, is well suited to the concentrations already permitted by the U.S. Food and Drug Administration, which limits use of ethoxyquin as a preservative in animal feeds to a maximum concentrations up to 150 ppm by weight.

By adding the ethoxyquin to the feed shortly prior to feeding as discussed above, the apparent disappearance of ethoxyquin, perhaps due to oxidation, may be able to be avoided. Thus, the desired ethoxyquin concentrations are not just initial concentrations in the feed, but in the preferred embodiment, the unoxidized ethoxyquin concentration of feed as it is ingested by the animal.

It is believed that the concentrations of ethoxyquin found to be effective with respect to cattle may be employed with other animals with similar results. Moreover, it is believed that the preferred ranges found with cattle, and particularly the optimum range, would be desirable for other animals as well. To the extent optimal dosages vary from species to species, however, optimization may be readily ascertained by those of ordinary skill in the art.

The ethoxyquin may be used as the sole shelf life enhancement aid, or it may be used in tandem with another technique or additive. For example, if desired, the ethoxyquin might be used in combination with Vitamin E, at a relative ethoxyquin to Vitamin E ratio of choice. Alternatively, or in addition, the resulting food product may be treated. For instance, potassium sorbate may be added to meat to inhibit bacterial spoilage.

For treating stressed mammals, the ethoxyquin should be incorporated into the feed of the mammals for a period beginning shortly prior to the stress-inducing actvity or, preferably, just after that activity. Thus, for receiving cattle, the treatment should begin shortly prior to shipment or, preferably, soon (if not immediately) after arrival of the calves to the feed yard (say, within a week after, preferably within two days after, optimally within a day after shipment) and extending for from about 14 to about 50 days (preferably about 28 to about 50 days, especially about 28 to about 42 days) reduces the incidence of morbidity, including respiratory disease and liver abscesses, improves the feed efficiency and weight gain of the cattle, and reduces the degree of offensiveness of the feces of the cattle. Although the treatment may be continued beyond 42 to 50 days, the economic advantages of doing so may diminish.

For increasing the shelf life of the meat, the ethoxyquin treatments preferably are applied during the finishing stage of the animal; that is, during the last period prior to slaughter. The treatment should be continued for a length of time sufficient for the resulting meat product to have an increased shelf life. It has been found that about 21 days is sufficient, but a treatment period of at least about 28 days is preferable. The treatment can be continued for as long as desired, but generally for meat products, treatment would not extend more than about 150 days.

The resulting meat product has been found to have an extended shelf life, and at a fraction of the cost of Vitamin E treatment. For example, ground beef may have a shelf life of ten to fourteen days as opposed to three to four days for ground beef from untreated cattle. Similarly, it is believed that increases in shelf life would be associated with other meats and dairy products as well. In addition, beef treated by the method of this invention has been found to appear younger than the meat from cattle of the same age, but untreated. This provides an additional significant advantage, as it allows desirable younger-colored beef to be obtained from chronologically older cattle. While not wishing to be bound to any particular theory, it is believed that this effect may be associated with the anti-oxidant nature of ethoxyquin, which may retard the aging process. Thus, it is believed that similar slowing of the aging process would be imparted to other animals receiving the treatment of this invention as well.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

Odor offensiveness of cattle feces was graded (on a scale from 1, representing least offensive, to 10, representing greatest offensiveness) by a team of assessors at six and thirty hours of age for control cattle and ethoxyquin-fed cattle. At six hours, the average score of the control cattle feces was 5.19, and for the ethoxyquin-fed cattle was 4.19. At thirty hours, the average score of the control cattle feces was 5.17, and for the ethoxyquin-fed cattle was 5.00.

EXAMPLE 2

Ninety-six mixed breed heifer calves (about 206 kg each) were purchased at sale barns by an order buyer and delivered as one group to a research facility and allocated randomly within eight weight blocks to treatment, with six heifers in each of sixteen pens, for a total of 48 heifers per treatment. Upon arrival, all heifers were fed for 42 days a totally mixed ration containing 30% cottonseed hulls, 53% cracked corn, and 11% soybean meal for 42 days. Treatments consisted of 0 or 150 mg of ethoxyquin per kilogram of diet. The heifers were observed daily for signs of mobidity. Of the group treated with ethoxyquin, 73% became sick, compared to 83% which became sick in the group whose diet did not contain ethoxyquin, representing a 12% reduction in morbidity. The reduced morbidity associated with the ethoxyquin intake was noted particularly with respect to respiratory disease. The corresponding medication cost for the ethoxyquin-treated calves was $5.75 per pen, versus $8.63 per pen for the calves that did not receive ethoxyquin representing a 33% reduction. No significant differences between the two sets of calves were noted with respect to the number of calves suffering recurrent sickness, the day of occurence of the first illness, average daily weight gain, daily feed intake or weight gain per quantity of feed intake, although this could be because the small sample size requires a difference to be substantial to be significant.

Over the first fourteen days of treatment, the control calves (those fed no Ethoxyquin) lost an average of 0.01 lb./day, while the calves whose feed contained 150 ppm by weight Ethoxyquin gained an average of 0.50 lb./day. Over the first 26 days of treatment, the control calves gained an average of 1.78 lb./day, while the calves whose feed contained 150 ppm by weight Ethoxyquin gained an average of 1.97 lb./day, a 10.8% improvement. Over the entire 42 days of treatment, the control calves gained an average of 1.88 lb./day, while the calves whose feed contained 150 ppm by weight Ethoxyquin gained an average of 1.96 lb./day, a 4.4% improvement. One of the control calves died (2.1%), while none of the Ethoxyquin-fed calves did.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed:

1. A method for treatment of stressed ruminant mammals to improve the collective health, feed efficiency or weight gain of the mammals, comprising feeding to the mammals a diet of feed comprising a substituted 1,2-dihydroquinoline compound of the formula

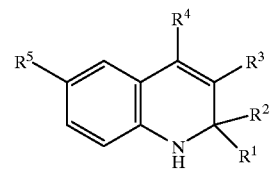

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, the diet being continued for a period of time, and the feed comprising the substituted 1,2-dihydroquinoline compound in an amount, sufficient to improve the collective health, feed efficiency or weight gain of the mammals.

2. A method as set forth in claim 1 wherein the substituted 1,2-dihydroquinoline compound is 6-ethoxy-1,2-dihydro-2,2,4-trimethylquinoline.

3. A method as set forth in claim 2 wherein the feed comprises greater than 50 ppm by weight 6-ethoxy-1,2-dihydro-2,2,4-trimethylquinoline.

4. A method as set forth in claim 3 wherein the feed comprises at most about 1,000 ppm by weight 6-ethoxy-1,2-dihydro-2,2,4-trimethylquinoline.

5. A method as set forth in claim 2 wherein the mammals are selected from the group consisting of cattle and sheep.

6. A method as set forth in claim 5 wherein the mammals are cattle.

7. A method for treating ruminant mammals undergoing a stress-inducing activity to inhibit morbidity resulting from the stress induced by the activity, comprising feeding to the mammals a diet of feed comprising a substituted 1,2-dihydroquinoline compound of the formula

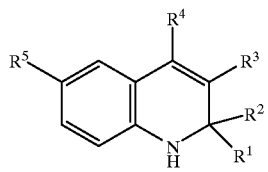

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, the diet being continued for a period of time, and the feed comprising the substituted 1,2-dihydroquinoline compound in an amount, sufficient to inhibit morbidity resulting from the stress.

8. A method as set forth in claim 7 wherein the mammals are fed the diet prior to undergoing the stress-inducing activity.

9. A method as set forth in claim 8 wherein the mammals are fed the diet commencing within one week after undergoing the stress-inducing activity.

10. A method for treatment of receiving cattle to improve the collective health, feed efficiency, weight gain or fecal odor of the receiving cattle, comprising feeding to the receiving cattle a diet of feed comprising a substituted 1,2-dihydroquinoline compound of the formula

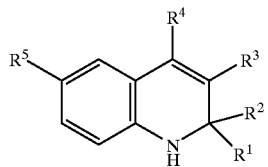

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, the diet being continued for a period of time, and the feed comprising the substituted 1,2-dihydroquinoline compound in an amount, sufficient to improve the collective health, feed efficiency or weight gain of the receiving cattle.

11. A method as set forth in claim 10 wherein the substituted 1,2-dihydroquinoline compound is 6-ethoxy-1,2-dihydro-2,2,4-trimethylquinoline.

12. A method as set forth in claim 11 wherein the feed comprises greater than 50 ppm by weight 6-ethoxy-1,2-dihydro-2,2,4-trimethylquinoline.

13. A method as set forth in claim 12 wherein the feed comprises at most about 1,000 ppm by weight 6-ethoxy-1,2-dihydro-2,2,4-trimethylquinoline.

14. A method as set forth in claim 11 wherein the diet is initiated prior to shipment of the receiving cattle to a feed yard and the period of time is from about 14 to about 42 days.

15. A method as set forth in claim 11 wherein the diet is initiated within one week after the receiving cattle are shipped to a feed yard and the period of time is from about 14 to about 42 days.

16. A method as set forth in claim 15 wherein the diet is initiated within one day after the receiving cattle are shipped to a feed yard.

17. A method as set forth in claim 10 wherein the collective health of the receiving cattle is improved.

18. A method as set forth in claim 17 wherein the collective health is improved as measured by a reduced incidence of morbidity of the receiving cattle.

19. A method as set forth in claim 10 wherein the feed efficiency of the receiving cattle is increased.

20. A method as set forth in claim 10 wherein the rate of weight gain of the receiving cattle is increased.

21. A method as set forth in claim 10 wherein the fecal odor of the receiving cattle is improved.

* * * * *